(12) United States Patent
Ernsperger et al.

(10) Patent No.: US 8,976,238 B2
(45) Date of Patent: Mar. 10, 2015

(54) OPTICAL OBSERVATION APPARATUS WITH MULTI-CHANNEL DATA INSERTION

(75) Inventors: Stefan Ernsperger, Schwaebisch Gmuend (DE); Gerhard Gaida, Aalen (DE)

(73) Assignee: Carl Zeiss Meditec AG (DE)

( * ) Notice: Subject to any disclaimer, the term of this patent is extended or adjusted under 35 U.S.C. 154(b) by 504 days.

(21) Appl. No.: 12/997,334

(22) PCT Filed: Jun. 9, 2009

(86) PCT No.: PCT/EP2009/004403
§ 371 (c)(1),
(2), (4) Date: Mar. 3, 2011

(87) PCT Pub. No.: WO2009/149961
PCT Pub. Date: Dec. 17, 2009

(65) Prior Publication Data
US 2011/0141262 A1    Jun. 16, 2011

(30) Foreign Application Priority Data
Jun. 13, 2008  (DE) .......................... 10 2008 028 482

(51) Int. Cl.
*H04N 7/18*  (2006.01)
*G02B 21/36*  (2006.01)
(Continued)

(52) U.S. Cl.
CPC .......... *G02B 21/361* (2013.01); *A61B 19/5223* (2013.01); *G02B 21/0004* (2013.01); *A61B 19/56* (2013.01); *G02B 21/22* (2013.01)
USPC .......................................................... 348/79

(58) Field of Classification Search
CPC ............... A61B 19/5223; A61B 19/56; G02B 21/0004; G02B 21/22; G02B 21/361
See application file for complete search history.

(56) References Cited

U.S. PATENT DOCUMENTS 4,786,154 A * 11/1988 Fantone et al. ............... 359/369
5,867,308 A    2/1999 Pensel
(Continued)

FOREIGN PATENT DOCUMENTS

DE    19911145    9/1999

OTHER PUBLICATIONS

English-language translation of Written Opinion of the International Searching Authority.

*Primary Examiner* — Dave Czekaj
*Assistant Examiner* — Md Haque
(74) *Attorney, Agent, or Firm* — Gerald E. Hespos; Michael J. Porco; Matthew T. Hespos

(57) ABSTRACT

An optical observation apparatus has an optical image channel for viewing optical field-of-view images, a processing unit to generate a first electronic insertion image via a first electronic image channel, and a data insertion image projector for generating an optical insertion image from the first electronic insertion image and inserting that image into the optical field-of-view image. An acquisition device acquires the optical field-of-view image without the optical insertion image inserted by the data insertion image projector. A second electronic image channel has a superimposition module, that superimposes the electronic field-of-view image with an electronic insertion image and provides the superimposed images via the second electronic image channel. The processing unit generates a second electronic insertion image, provides available display data elements, and makes it possible to assemble the electronic insertion images and assign them to different electronic image channels.

14 Claims, 5 Drawing Sheets

(51) Int. Cl.
*A61B 19/00* (2006.01)
*G02B 21/00* (2006.01)
*G02B 21/22* (2006.01)

(56) References Cited

U.S. PATENT DOCUMENTS

| | | | |
|---|---|---|---|
| 5,982,532 A | 11/1999 | Mittelstadt | |
| 6,005,710 A | 12/1999 | Pensel | |
| 6,081,371 A | 6/2000 | Shioda | |
| 6,268,957 B1 | 7/2001 | Hoover | |
| 7,050,225 B2 * | 5/2006 | Nakamura | 359/368 |
| 7,580,185 B2 | 8/2009 | Haisch | |
| 7,649,681 B2 | 1/2010 | Hauger | |
| 7,688,503 B2 | 3/2010 | Hermann | |
| 8,221,304 B2 * | 7/2012 | Shioda et al. | 600/102 |
| 2003/0112509 A1 | 6/2003 | Takahashi | |
| 2003/0181803 A1 | 9/2003 | Sander | |
| 2004/0109231 A1 | 6/2004 | Haisch | |
| 2008/0013166 A1 | 1/2008 | Haisch | |
| 2010/0097618 A1 | 4/2010 | Haisch | |

* cited by examiner

FIG 3
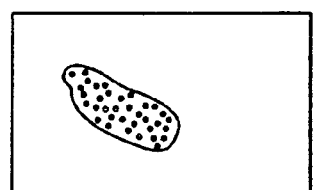
50
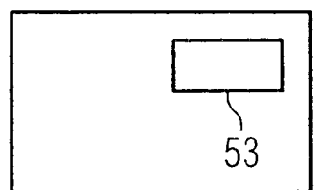
53
52
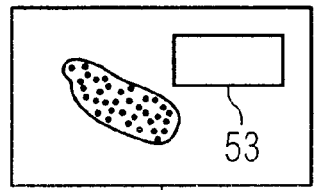
53
54
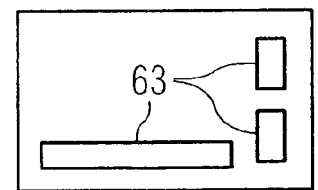
63
62
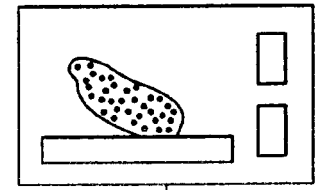
64
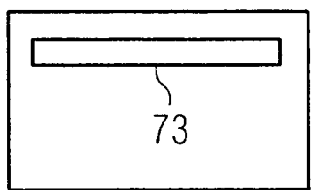
73
72
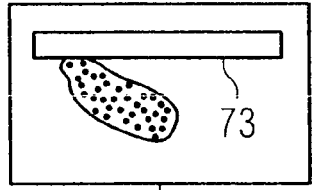
73
74

OPTICAL OBSERVATION APPARATUS WITH MULTI-CHANNEL DATA INSERTION

BACKGROUND OF THE INVENTION

1. Field of the Invention

The invention relates to an optical observation apparatus, in particular a surgical microscope comprising a superimposition device for superimposing the optical image with an insertion image. In addition, the invention relates to a method for the insertion of electronic insertion images into an optical observation apparatus, in particular into a surgical microscope.

2. Description of the Related Art

Insertion images are inserted in particular into the beam path of surgical microscopes in order to convey additional treatment-relevant information to the treating physician. Insertion images can be e.g. the result of a contour finder, a reference axis, a reference angle, apparatus parameters such as, for instance, the magnification factor or the diaphragm aperture, or patient-related data.

The published US patent application US 2003181803 discloses a surgical microscope having an electronic unit and a superimposition module. In this case, patient data are communicated from the electronic unit to the superimposition module, which inserts the data into the surgeon's field of view.

Furthermore, surgical microscopes comprising a camera device are known which detect the surgeon's field of view by virtue of there being arranged in the beam path of the microscope a beam splitter or a similar image coupling-out device that forwards the field of view to a video camera for acquiring the video images.

Such a system, which simultaneously permits the insertion of patient data, is presented in US patent specification U.S. Pat. No. 7,050,225 B2. In this case, what is inherent to this solution is that the image acquired by the video camera always shows the overall representation such as corresponds to the actual field of view of the surgeon, that is to say with all the patient data inserted by the superimposition module.

The published German patent application DE 102 43 852 A1 discloses a further microscopy system, which enables a stereomicroscopic image to be superimposed with an electronically generated image, wherein the electronically generated image is an electronic superimposition of an input image dependent on the chosen magnification or the rotational position of the zoom system with an input image that is independent of the chosen magnification or the rotational position of the zoom system.

DE 101 01 184 A1 describes a surgical microscope comprising an observation tube and a camera for recording the observation image. A monitor for representing the recorded observation image is additionally present. In the surgical microscope, an electronic insertion image can both be inserted into the beam path by means of an image projection module and be mixed with the image recorded by the camera by means of an image mixer and the mixed image can be represented on the monitor.

Against the background of this prior art, it is an object of the present invention to provide an advantageous optical observation apparatus, in particular an advantageous surgical microscope. It is a further object of the present invention to provide an advantageous method for the insertion of electronic insertion images into an optical observation apparatus, in particular into a surgical microscope.

SUMMARY OF THE INVENTION

An optical observation apparatus according to the invention comprises at least one optical image channel for viewing an optical field-of-view image from an operation site, a processing unit, which is designed to generate a first electronic insertion image and to provide the first electronic insertion image via a first electronic image channel, and an optical data insertion image projector which is connected to the processing unit via the first electronic image channel and serves for generating an optical insertion image from the first electronic insertion image and a superimposition device for inserting the generated optical insertion image into the optical field-of-view image generated by the optical image channel. In addition, the optical observation apparatus comprises an image acquisition device for electronically acquiring the optical field-of-view image from the optical channel and for generating an electronic field-of-view image, wherein the image acquisition device is arranged and/or embodied in such a way that it acquires the optical field-of-view image without the optical insertion image inserted by the data insertion image projector, and at least one second electronic image channel, which comprises an electronic image superimposition module, which is designed to superimpose the electronic field-of-view image with an electronic insertion image and to provide the electronic field-of-view image with the superimposed electronic insertion image via the second electronic image channel.

According to the invention, the processing unit is configured for generating at least one second electronic insertion image. Moreover, the processing unit has a configuration module or is connected to a configuration module which is designed to provide a selection of available display data elements, and makes it possible in each case freely to assemble the first electronic insertion image and the second electronic insertion image from the display data elements and to assign the electronic insertion images to different electronic image channels.

The invention is based on the insight that in the prior art all observers receive the same image information. Although in DE 102 43 852 A1 the insertion images for different tubes of a surgical microscope are in each case adapted to the chosen magnification or the rotational position of the zoom system, the images contain the same information in each case.

For different applications, however, it would be desirable if insertion images containing different information could be made available, for instance for a separate screen representation of the operation site for training purposes, or in order to record the operation procedure. Moreover, data insertions other than those for the surgeon may be desired for such video recordings, such as, for instance, date, time of day, and specific treatment parameters, which are not required by the surgeon during the intervention, or are even a hindrance. It is likewise conceivable that in the case of e.g. in the case of a surgical microscope comprising primary and secondary tubes, different data insertions than in the primary tube are desired in the secondary tube.

This is the starting point of the invention, and the invention affords a free configurability of the electronic insertion images provided for the electronic image channels. In particular, the first electronic insertion image can have a first selection of display data elements, whereas the second insertion image can have a second selection of display data elements, which is at least partly different from the first selection of display data elements. It goes without saying that the optical observation apparatus according to the invention also affords the possibility of making identically configured insertion images available to all the electronic image channels, as heretofore.

This makes it possible, for example, to generate a first insertion image for the primary user and a second insertion image for secondary users. These can be specifically adapted for the respective intended purpose. By way of example, the invention makes it possible, firstly, to make available to a surgeon operation-relevant additional information such as preoperatively created images (for instance from computed tomography or magnetic resonance tomography) or images from further sources such as endoscopes, in addition or as an alternative to the operation site. Secondly, however, the invention also makes it possible to display a different selection of additional information on monitors together with the electronic field-of-view image, for instance for the further operation personnel or for a recording. Moreover, it is possible to make available different sets of inserted additional information for a plurality of parallel recordings. The sets of additional information (display data elements) can be compiled for this purpose by the factory or by the operator by a process in which display data elements that are intended to be represented in a data display in the insertion image are selected and then assigned to one or a plurality of electronic image channels.

By virtue of the fact that the image acquisition device, for example a video camera, is embodied or arranged in such a way that the electronic field-of-view image the view of the operation site as chosen by the user, for example a surgeon, is acquired without additionally inserted information, the database is generated for further representations (with their respective insertions) which are provided by the system.

The optical observation apparatus according to the invention thus increases the flexibility in the insertion of additional information by comparison with the prior art.

The optical observation apparatus can be developed to the effect that it has a first optical channel and a second optical channel in parallel with the first, wherein the data insertion image projector is arranged in the first optical channel and the image acquisition device is arranged in the second optical channel. Consequently, the beam path is not unnecessarily impaired by the fact that firstly the image acquisition device and secondly the data insertion image projector are arranged one behind the other in the beam path. Moreover, the camera in this arrangement cannot concomitantly record the optical insertion image, such that the optical field-of-view image is acquired without the optical insertion image inserted by the data insertion image projector.

It is also possible, however, for the image acquisition device to be disposed upstream of the data insertion image projector in the direction of the operation site, that is to say to be situated between the data insertion image projector and the objective. In that case, too, the camera in this arrangement cannot concomitantly record the optical insertion image, such that the optical field-of-view image is acquired without the optical insertion image inserted by the data insertion image projector. If the optical observation apparatus comprises a first optical channel and a second optical channel in parallel with the first, a first image acquisition device, a second image acquisition device, a first data insertion image projector and a second optical superimposition device can be present. The image acquisition devices are then disposed upstream of the data insertion image projectors in the direction of the operation site. As a result, stereoscopic images can also be coupled out, and a stereoscopic insertion image can be generated, for instance in order to insert three-dimensional representations.

In one development of the optical observation apparatus, the electronic field-of-view image and/or the first electronic insertion image and/or the second electronic insertion image is an image of a sequence of images that form a video sequence. In this case, the image sequence can contain frames and/or fields, wherein the superimposition device in embodiments can be designed to carry out the superimposition on frames.

Furthermore, the optical observation apparatus can contain a data management module coupled to the configuration module, said data management module being designed for storing and/or providing display data elements. This makes it possible to separate functions of data provision and data management functionally relative to the image processing functions and general operating functions of the apparatus, such that firstly the performance of the data handling and secondly the expandability of the system are improved. In such an embodiment, the configuration module can be designed to determine the selection of available display data elements by interrogating the data management module.

Furthermore, the configuration module can be designed to generate at least one menu control element, and the processing unit can be designed to generate the insertion image with inclusion of the menu control element. As a result, it is possible to provide menu-guided operation firstly for the configuration and user-implemented definition of the assignments of display data elements to electronic image channels with possibly subsequent storage of the assignment in a configuration memory, and also menu controls for the observation operation mode of the optical observation apparatus.

The invention additionally provides a method for the insertion of electronic insertion images into an optical observation apparatus, in particular into a surgical microscope, wherein the optical observation apparatus is equipped with at least one optical image channel for viewing an optical field-of-view image from an operation site, a first electronic image channel, at least one second electronic image channel, a data insertion image projector, which is connected to the first electronic image channel and serves for generating an optical insertion image from an electronic insertion image, and an image acquisition device for electronically acquiring the optical field-of-view image, wherein the image acquisition device is arranged and/or embodied in such a way that it acquires the optical field-of-view image without the optical insertion image inserted by the data insertion image projector.

The method comprises the following steps:
generating at least one first electronic insertion image,
generating an optical insertion image from the first electronic insertion image,
inserting the generated optical insertion image into the optical field-of-view image,
electronically acquiring the optical field-of-view image, wherein the optical field-of-view image (50) is acquired without the optical insertion image inserted by the data insertion image projector,
generating an electronic field-of-view image from the acquired optical field-of-view image,
superimposing the electronic field-of-view image with an electronic insertion image, and
outputting the electronic field-of-view image superimposed with the electronic insertion image.

In the method according to the invention, the electronic insertion image with which the electronic field-of-view image is superimposed is a second electronic insertion image. Moreover, a selection of available display data elements is made available, wherein each electronic insertion image is freely configurable on the basis of the display data elements made available. Each configured electronic insertion image is individually assigned to one of the image channels.

The effects and advantages that have already been described with reference to the optical observation apparatus are obtained with the method according to the invention. In particular, a first selection of display data elements can be inserted into the first electronic insertion image and a second selection of display data elements can be inserted into the second electronic insertion image, said second selection being at least partly different from the first selection of display data elements. Furthermore, the electronic field-of-view image and/or the first electronic insertion image and/or the second electronic insertion image can be in each case an image from a sequence of images that form a video sequence.

The selection of available display data elements can be effected with generation and processing of an interrogation. Moreover, a menu control element can be generated and the insertion image can be inserted with inclusion of the menu control element.

The method according to the invention can additionally comprise the following steps: determining a selection of available electronic image channels; determining a selection of available display data elements and providing the determined display data elements and the determined image channels for the free configuration of the electronic insertion images. In this way, it is possible to ensure that only the electronic image channels of apparatuses that are actually connected and the display data elements provided therefor are ever available for configuration, but not those of apparatuses that are connectable, but actually not connected. The configuration interface can thus be made clearer than if the image channels and display data elements of all connectable apparatuses are always offered.

Further features, properties and advantages of the present invention will become apparent from the following description of exemplary embodiments with reference to the accompanying figures.

BRIEF DESCRIPTION OF THE DRAWINGS

FIG. 3 shows the field-of-view image, insertion images and corresponding superimposed images.

DETAILED DESCRIPTION OF THE PREFERRED EMBODIMENTS

Figure 1:
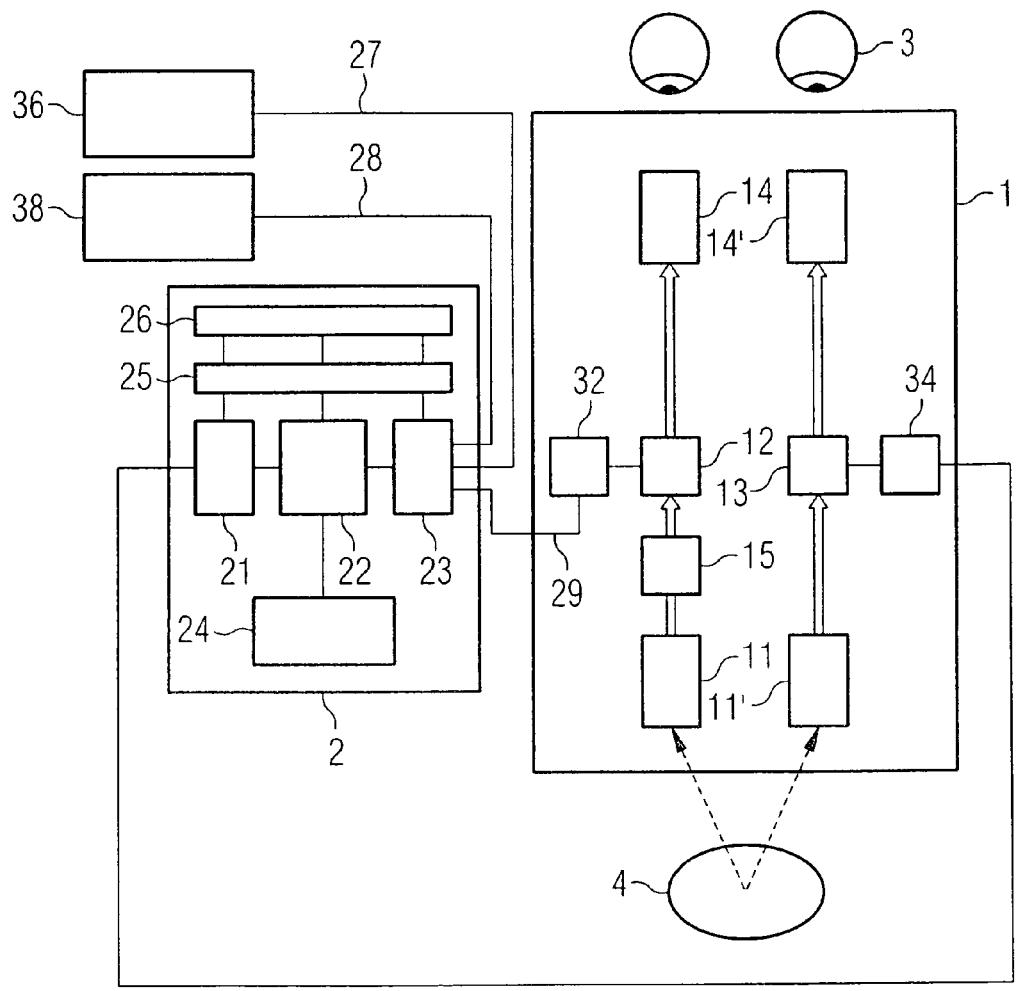
FIG. 1 shows a schematic block diagram of a surgical microscope as a first exemplary embodiment of an optical observation apparatus according to the invention.

FIG. 1 shows a schematic block diagram of an exemplary embodiment of the invention, in which the optical observation apparatus is embodied as a surgical microscope. Alternatively, it could also be embodied as an endoscope, for example.

The surgical microscope in the exemplary embodiment comprises an optical subsystem 1 and an electronic subsystem 2. In the optical subsystem 1, an observer 3 views the operation site 4 through a first optical image channel, which has a first objective optical unit 11, an optical superimposition device 12 and a first eyepiece optical unit 14, and also a second optical image channel, which is in parallel with the first optical image channel and has a second objective optical unit 11', a beam splitter 13 and a second eyepiece optical unit 14'. The superimposition device 12 and/or the beam conductor 13 can be realized e.g. as a partly transmissive mirror or as prisms. The objective optical units 11 and 11', the superimposition device 12 and the beam splitter 13, and also the eyepiece optical units 14 and 14' form the optical subsystem 1 of the surgical microscope.

Furthermore, a video camera 34 for acquiring the optical field-of-view image coupled out from the beam path of the second optical observation channel by the beam conductor 13 and for converting said field-of-view image into an electronic field-of-view image is present in the optical subsystem 1. The camera 34 has a signal system connected to the electronic subsystem 2.

For converting an electronic insertion image into an optical insertion image, a data insertion image projector 32 (abbreviated to DI image projector hereinafter) is present in the optical subsystem 1. The optical insertion image generated by the DI image projector 32 can be inserted into the beam path of the first optical image channel via the superimposition device 12. By way of example, transmitted-light or reflected-light LCD displays or digital mirror devices (DMD) can be employed as DI image projector 32. A shutter 15 can additionally be present between the objective 11 and the superimposition device of the optical subsystem 1, by means of which shutter the optical image of the first optical channel can be masked out in favor of the image provided by the DI image projector 32. The video camera 34 and the DI image projector 32 can also be assigned to the electronic subsystem 2 instead of to the optical subsystem 1 as in the present exemplary embodiment.

The electronic subsystem 2 comprises a processing unit (processor) 22 with a video data input interface 21 connected thereto and with a video data output interface 23 likewise connected to the processing unit 22. Furthermore, the electronic subsystem contains an image superimposition unit 24 connected to the processing unit 22. In addition, a configuration module 25 is connected to the processing unit 22, the input interface 21 and the output interface 23, said configuration module in turn being connected to a data management module 26.

The electronic subsystem 2 is linked by a video data input of the input interface 21 to the optical subsystem, namely the signal output of the video camera 34, and is linked by a respective video data output of the output interface 23 to the DI image projector 32, an operation control monitor 36 and to a video data recording apparatus 38. In the present exemplary embodiment, therefore, the electronic subsystem 2 physically provides, via its output interface 23, three electronic image channels, which in FIG. 1 are furthermore represented by the connection between interface 23 and image projector 32 (first image channel 29), the connection between interface 23 and control monitor 36 (second image channel 27) and the connection between interface 23 video data recording apparatus 38 (third image channel 38) and. These physical electronic image channels respectively correspond to a logical image channel which is managed and addressed by the processing unit 22 and further components of the electronic subsystem 2.

In the present embodiments, the first image channel 29 constitutes a data transfer channel, wherein the image to be projected is first generated in the image projector 32 and the output interface 23 merely supplies the data to be displayed in a non-graphical data format. Alternatively, however, it is also possible for the insertion image that is to be coupled in optically to be output via the processing unit 22 electronically in a graphical format and be first generated in the DI image projector.

Figure 2:
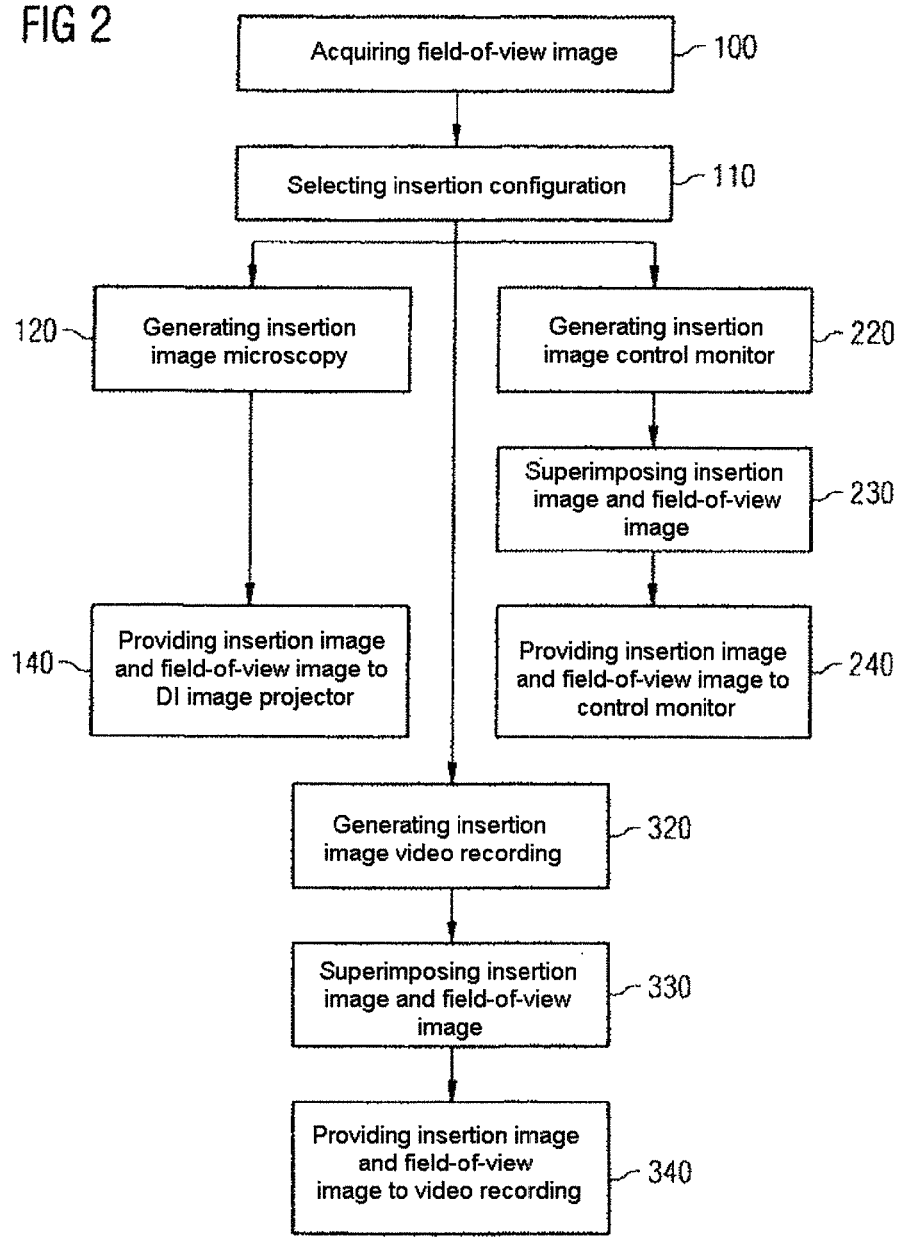
FIG. 2 shows a schematic overview of the method according to the invention and its steps.

The functioning of the device is explained below in connection with FIG. 2 and the associated method. FIG. 2 shows a schematic overview of the method and its steps.

If a surgeon views the operation site by selection of a specific field of view by setting the surgical microscope and its optical unit, the beam splitter 13 splits out part of the optical field-of-view image appearing in the beam path and directs it onto the video camera 34.

In step 100, the camera 34 acquires individual images, or film-like image sequences consisting of fields and/or frames, and supplies them as an electronic field-of-view image in the form of an analog or digital signal to the video data input 21, which preconditions the data and forwards the electronic field-of-view image to the processing unit 22 for further processing.

In step 110, the processing unit 22 then selects an insertion configuration defined by the user, which, in the present example, determines a first set of display data elements with additional information for the surgeon, a second set of display data elements with additional data and menu control elements for the control monitor, and a third set of display data elements with additional information for the recording device. In this case, the sets of additional information and, if appropriate, control elements can be at least partly different from one another. In this case, the insertion configuration can be stored in a configuration file or an equivalent configuration memory and be read out in step 110. In addition, prior to the application of the stored configuration, the availability of the display data elements which are used in the configuration and which are intended to be represented in the insertion image in the inserted data displays can be checked, and so can the availability of the electronic image channels 27, 28, 29 used in the configuration. Furthermore, alternatively or together with the defined, stored insertion configuration, an insertion configuration can also be defined by the user during the operation of the system, which insertion configuration can then also be stored as a defined insertion configuration. This will be described in greater detail below with reference to FIG. 4.

The following sequences of steps 120 to 140, 220 to 240 and 320 to 340 can be performed in parallel with one another, or with suitable prioritization section by section or fully sequentially.

In step 120, the processing unit 22 generates a first electronic insertion image with a first set of additional information and in step 140 outputs it via the first image channel 29 to the DI image projector 32. The latter generates an optical insertion image, that is to say a light pattern, which is correspondingly reflected via the optical superimposition device 12 into the beam path of the first optical channel, such that the optical field-of-view image appears with the inserted additional information.

In step 220, the processing unit 22 generates a second electronic insertion image with the second set of additional information and menu control elements. In order that not just the insertion image but also the optical field-of-view image appears on the image monitor 36, the image superimposition unit 24 superimposes the electronic field-of-view image with the second electronic insertion image in step 230. In step 240, the electronic field-of-view image superimposed with the electronic insertion image is then forwarded by the processing unit to the output interface 23, which outputs it via the second electronic image channel 27 to the control monitor 36.

In step 320, the processing unit 22 generates a third electronic insertion image, then with the third set of additional information as desired for video recording. In step 330, the image superimposition device 24 superimposes the acquired electronic field-of-view image with the third insertion image. In step 340, the processing unit 22 then forwards the electronic image produced during the superimposition to the output interface 23, which outputs it via the third electronic image channel 28 to the video recording device 38.

All acquired, generated and superimposed images can be both individual images and fields or frames of a video data stream (e.g. I and P frames of an MPEG-2 data stream). Electronic images provided can be realized in a digital image format, also in compressed fashion, or alternatively or simultaneously be present as an analog image signal. Particularly with regard to a menu control realized by means of the second insertion image, the insertion image can constantly change depending on the control state of the processing unit 22.

In embodiments, the processing unit can be realized by a video grabber unit of the processing unit 22 receiving the video signal with the field-of-view image from the input interface 21 and then extracting the fields. The fields can then be combined into frames in frame memories of the processing unit 22, wherein a dedicated frame memory can be formed for each image channel 27, 28, 29 via which a specific superimposed image is intended to be provided. The superimposition unit can contain an overlay memory, into which the processing unit inputs the generated electronic insertion image (once again a separate memory per image channel is possible), such that the superimposition unit can combine the content of each of the overlay memories in each case with the content of the corresponding frame memory in order to carry out the actual superimposition. Afterward, in order to obtain an analog video signal, a digital/analog conversion can be carried out, or the frames can be MPEG-2-coded and passed on digitally.

FIG. 3 shows examples of a field-of-view image, insertion images and corresponding superimposed images.

The image 50 represents the optical field-of-view image of the surgeon such as would be seen by the latter entirely without insertions through the microscope. Consequently, this image is visually identical to the electronic field-of-view image as obtained via the video camera 34. A first electronic insertion image 52 comprising the first set of additional information (data display window 53) is generated for the surgeon. Said insertion image is passed on to the DI image projector 32, such that overall the representation of the image 54 arises when the operation site is viewed through the microscope.

A second electronic insertion image 62 having the second set of additional information and menu control elements 63 is correspondingly generated for the control monitor 36. This insertion image is electronically combined with the electronic field-of-view image 50, such that the superimposed electronic image 64 arises.

A third electronic insertion image 72 containing data displays 73 relevant to recording as a third set of additional information is analogously generated for video recording. In this case, too, the insertion image is electronically combined with the electronic field-of-view image 50, such that the superimposed electronic image 64 arises.

Figure 4:
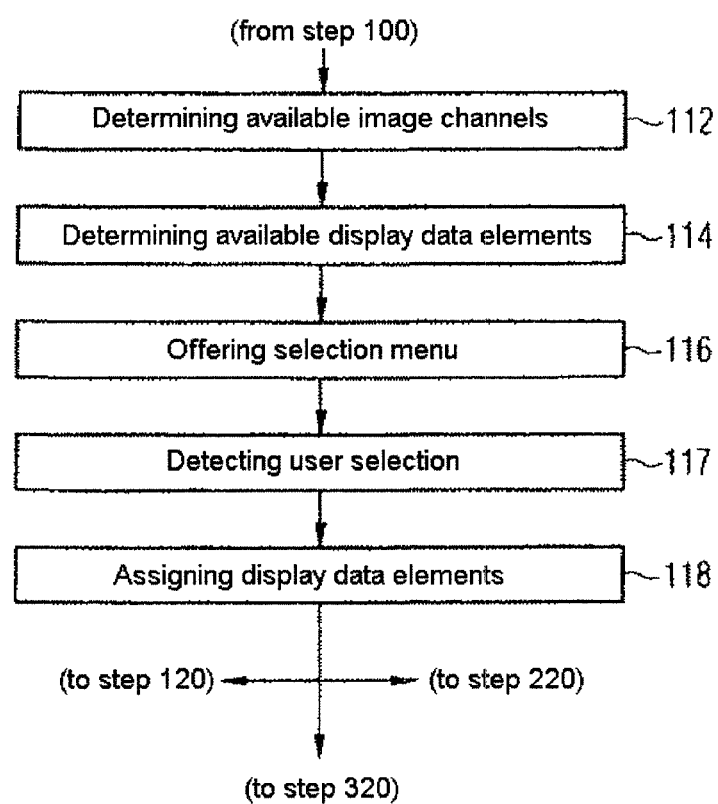
FIG. 4 shows a detail of an embodiment variant of the method illustrated in FIG. 2.

FIG. 4 shows in detail the configuration or assignment of additional information (display data elements) in step 110 in FIG. 2. Firstly, in step 112, the configuration module 25 determines the available electronic image channels. For this purpose, the configuration module 25 can access the output interface 23. The result is a selection of available electronic image channels 27, 28, 29 via which electronic field-of-view images superimposed with electronic insertion images, or only insertion images as such, can be provided to other system components or toward the outside. The configuration module 25 then determines the available display data elements in step 114. For this purpose, it can access the data management module 26, which stores and/or manages and/or provides the display data elements. Such display data elements can originate from preceding measurement, endoscopy or imaging procedures, for instance. As the result, the configuration module 25 obtains a selection of available display data elements which are available, in principle, for insertion as additional information in insertion images.

It is then possible to call up from a configuration file an existing assignment of display data elements to electronic image channels 27, 28, 29, which can be stored in the configuration module or in the data management module. On the basis of the determination of available channels and data elements, the configuration module 25 can check whether the system configuration has changed and whether the stored configuration can be applied. If a manual assignment by the user is not provided, the assignment is performed by the configuration module in accordance with the configuration file in step 118 and the insertion images are correspondingly generated and superimposed in steps 120 ff., 220 ff. and 320 ff.

However, if an assignment is intended to be effected by the operator, then in step 116 the configuration module generates a selection menu, which is supplied as an insertion image to the control monitor via one of the electronic image channels 27, for example. In step 117, the assignments made by the user on the control monitor are correspondingly acquired by the configuration module 25, and the assignment is correspondingly performed in step 118. The assignments made by the user can then be stored in a configuration file.

The present system and its functional units which carry out the method can be realized at least partly in hardware, software or combinations thereof, for example using specific image processing processors and cards and embedded software.

Figure 5:
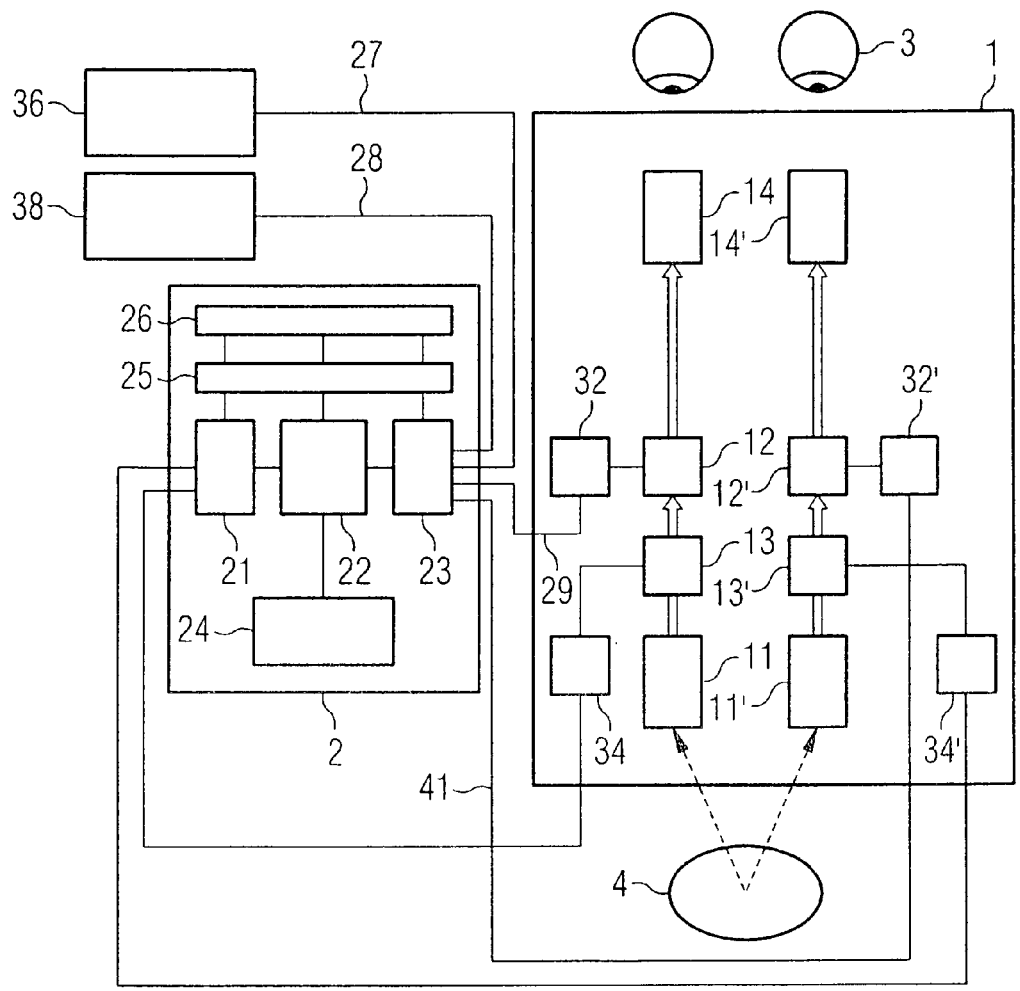
FIG. 5 shows a schematic block diagram of a second exemplary embodiment of the optical observation apparatus.

A second exemplary embodiment of the optical observation apparatus according to the invention is shown in FIG. 5. The figure shows a surgical microscope that is largely identical to that in FIG. 1. Elements which are identical with those from FIG. 1 are designated in FIG. 5 by the same reference numerals as in FIG. 1 and will not be described again.

The only difference between the surgical microscope from FIG. 5 and the surgical microscope from FIG. 1 is that in FIG. 5 a DI image projector 32, 32' and a superimposition device 12, 12' and also a video camera 34, 34' and a beam splitter 13, 13' are present in each optical image channel. In this case, the beam splitters 13, 13' are arranged between the superimposition devices 12, 12' and the objective optical units 11, 11', such that the video cameras 34, 34' record the optical field-of-view image without inserted additional information. Moreover, in comparison with the surgical microscope from FIG. 1, a fourth electronic image channel 41 is present, which connects the output interface 23 to the second DI image projector 32'. The insertion of additional information in the form of stereographic insertion images becomes possible as a result.

In addition to the three electronic image channels illustrated in the exemplary embodiments, further image channels can also be present. On the other hand, however, the invention can also be realized with just two electronic image channels.

Appropriate peripheral devices that can be connected to the electronic subsystem 2 via an electronic image channel include DI image projectors, monitors and recording devices. Moreover, a plurality of optical image channels can be present which can be connected to the electronic subsystem 2 in each case via a dedicated electronic image channel, in order that insertion images with different items of additional information are made available to different observers.

The system described allows simultaneously a plurality of different compilations of additional information such as patient data, preoperative operation site recordings, date, etc., to be defined freely and flexibly, and these compilations to be assigned to different representation channels and the operation field of view to be displayed, recorded or processed further with the respectively inserted additional information via the different representation channels. As a result, the system becomes flexibly configurable, and its area of application is considerably extended without complex technical adaptations.

The invention claimed is:

1. An optical observation apparatus (1, 2) comprising
first and second optical image channels (11, 12, 14; 11', 13, 14') in parallel with one another for viewing an optical field-of-view image (50) from an operation site (4),
a processing unit (22) designed to generate a first electronic insertion image (52, 62) and to provide the first electronic insertion image (52, 62) via a first electronic image channel (29),
an optical data insertion image projector (32) arranged in the first optical image channel (11, 12, 14) and connected to the processing unit (22) via the first electronic image channel (29) and for generating an optical insertion image from the first electronic insertion image (52, 62) and for inserting the generated optical insertion image into the optical field-of-view image (50) generated by the first optical image channel (11, 12, 14),
an image acquisition device (34) arranged in the second optical image channel (11', 13, 14') for electronically acquiring the optical field-of-view image (50) from the second optical image channel (11', 13, 14') and for generating an electronic field-of-view image, wherein the image acquisition device (34) is arranged and/or embodied in such a way that it acquires the optical field-of-view image (50) without the optical insertion image inserted by the data insertion image projector (32), and
at least one second electronic image channel (27, 28) connected to an electronic image superimposition module (24) designed to superimpose the electronic field-of-view image with an electronic insertion image and to provide the electronic field-of-view image (64) with the superimposed electronic insertion image via the second electronic image channel (27, 28), characterized in that
the processing unit (22) is configured for generating at least one second electronic insertion image, and
the processing unit (22) has a configuration module (25) or is connected to a configuration module (25) that is designed to provide a selection of available display data elements (53, 63, 73), and makes it possible in each case freely to assemble the first electronic insertion image and the second electronic insertion image from the display data elements (53, 63, 73) and to assign the electronic insertion images to different electronic image channels (27, 28, 29).

2. A method for the insertion of electronic insertion images into an optical observation apparatus (1, 2), in particular into a surgical microscope, a processing unit (22), comprising first and second optical image channels (11, 12, 14; 11', 13, 14') in parallel with one another for viewing an optical field-of-view image (50) from an operation site (4), a first electronic image channel (29) and at least one second electronic image channel (27, 28), an optical data insertion image projector (32) connected to the first electronic image channel (29) for generating an optical insertion image from electronic insertion images (52, 62, 72), and an image acquisition device (34) for electronically acquiring the optical field-of-view image (50), wherein the image acquisition device (34) is arranged and/or embodied in such a way that it acquires the optical field-ofview image (50) without the optical insertion image inserted by the data insertion image projector (32), comprising the following steps:
- using the processing unit (22) for generating the electronic insertion images (52, 62),
- using the optical data insertion image projector (32) for generating an optical insertion image from at least one of the first electronic insertion images (52, 62, 72),
- using the optical data insertion image projector (32) for inserting the generated optical insertion image into the optical field-of-view image (50),
- using the image acquisition device (34) for electronically acquiring the optical field-of-view image (50), wherein the optical field-of-view image (50) is acquired without the optical insertion image inserted by the data insertion image projector (32),
- using the image acquisition device (34) for generating an electronic field-of-view image from the acquired optical field-of-view image (50),
- using an image superimposition unit (24) for superimposing the electronic field-of-view image with an electronic insertion image, and
- using the processing unit (22) for outputting the electronic field-of-view image superimposed with at least one of the electronic insertion images (52, 62, 72), characterized in that
- the electronic insertion image with which the electronic field-of-view image is superimposed is a second electronic insertion image,
- a selection of available display data elements (53, 63, 73) is made available, and
- each electronic insertion image (52, 62, 72) is freely configurable on the basis of the display data elements (53, 63, 73) made available,
- each configured electronic insertion image is individually assigned to one of the image channels (27, 28, 29).

3. The optical observation apparatus as claimed in claim 1, characterized in that the first electronic insertion image has a first selection of display data elements (53), and the second insertion image has a second selection of display data elements (63), which is at least partly different from the first selection of display data elements (53).

4. The optical observation apparatus as claimed in claim 1, characterized in that the electronic field-of-view image and/or the first electronic insertion image and/or the second electronic insertion image is an image of a sequence of images that form a video sequence.

5. The optical observation apparatus as claimed in claim 1, characterized in that a data management module (26) coupled to the configuration module (25) is included, designed for storing and/or providing display data elements (53, 63, 73).

6. The optical observation apparatus as claimed in claim 5, characterized in that the configuration module (25) is designed to determine the selection of available display data elements (53, 63, 73) by interrogating the data management module.

7. The optical observation apparatus as claimed in claim 1, characterized in that the configuration module (25) is designed to generate at least one menu control element (63), and the processing unit (22) is designed to generate the insertion image with inclusion of the menu control element.

8. The optical observation apparatus as claimed in claim 1, characterized by its configuration as a surgical microscope.

9. A method for the insertion of electronic insertion images into an optical observation apparatus (1, 2), in particular into a surgical microscope, a processing unit (22), comprising at least one optical image channel (11, 12, 14) for viewing an optical field-of-view image (50) from an operation site (4), a first electronic image channel (29) and at least one second electronic image channel (27, 28), an optical data insertion image projector (32) connected to the first electronic image channel (29) for generating an optical insertion image from electronic insertion images (52, 62, 72), and an image acquisition device (34) for electronically acquiring the optical field-of-view image (50), wherein the image acquisition device (34) is arranged and/or embodied in such a way that it acquires the optical field-of-view image (50) without the optical insertion image inserted by the data insertion image projector (32), comprising the following steps:
- using the processing unit (22) for generating the electronic insertion images (52, 62),
- using the optical data insertion image projector (32) for generating an optical insertion image from at least one of the first electronic insertion images (52, 62, 72),
- using the optical data insertion image projector (32) for inserting the generated optical insertion image into the optical field-of-view image (50),
- using the image acquisition device (34) for electronically acquiring the optical field-of-view image (50), wherein the optical field-of-view image (50) is acquired without the optical insertion image inserted by the data insertion image projector (32),
- using the image acquisition device (34) for generating an electronic field-of-view image from the acquired optical field-of-view image (50),
- using an image superimposition unit (24) for superimposing the electronic field-of-view image with an electronic insertion image, and
- using the processing unit (22) for outputting the electronic field-of-view image superimposed with at least one of the electronic insertion images (52, 62, 72), characterized in that
- the electronic insertion image with which the electronic field-of-view image is superimposed is a second electronic insertion image,
- a selection of available display data elements (53, 63, 73) is made available, and
- each electronic insertion image (52, 62, 72) is freely configurable on the basis of the display data elements (53, 63, 73) made available,
- each configured electronic insertion image is individually assigned to one of the image channels (27, 28, 29).

10. The method as claimed in claim 9, characterized in that the following steps are furthermore included:
- using a configuration module (25) for determining a selection of available electronic image channels (112),
- using the configuration module (25) for determining a selection of available display data elements (114), and
- using the configuration module (25) for providing the determined display data elements (114) and the determined image channels (112) for the free configuration of the electronic insertion images.

11. The method as claimed in claim 9, characterized in that a first selection of display data elements (53) is inserted into the first electronic insertion image, and in that a second selection of display data elements (63) is inserted into the second electronic insertion image, said second selection being at least partly different from the first selection of display data elements (53).

12. The method as claimed in claim 9, characterized in that the electronic field-of-view image and/or the first electronic insertion image and/or the second electronic insertion image is in each case an image of a sequence of images that form a video sequence.

13. The method as claimed in claim 9, characterized in that the selection of available display data elements (53, 63, 73) is effected with generation and processing of an interrogation.

14. The method as claimed in claim 9, characterized in that at least one menu control element is generated (116) and the insertion image is inserted with inclusion of the menu control element.

\* \* \* \* \*

UNITED STATES PATENT AND TRADEMARK OFFICE
CERTIFICATE OF CORRECTION

Page 1 of 1

PATENT NO. : 8,976,238 B2
APPLICATION NO. : 12/997334
DATED : March 10, 2015
INVENTOR(S) : Stefan Ernsperger and Gerhard Gaida It is certified that error appears in the above-identified patent and that said Letters Patent is hereby corrected as shown below:

Title page, item (75) Inventors: should read as follows:
Stefan Ernsperger, Ellwangen (DE);
Gerhard Gaida, Aalen (DE)

Signed and Sealed this
Twenty-eighth Day of July, 2015

Michelle K. Lee
*Director of the United States Patent and Trademark Office*